(12) United States Patent
Madsen et al.

(10) Patent No.: US 9,820,941 B2
(45) Date of Patent: Nov. 21, 2017

(54) SPLA2 HYDROLYSABLE LIPOSOMES WITH IMPROVED STORAGE STABILITY

(75) Inventors: Mogens Winkel Madsen, Virum (DK); Sune Allan Petersen, Greve (DK); Anders Falk Vikbjerg, Greve (DK)

(73) Assignee: Bio-Bedst ApS, Hørsholm (DK)

( * ) Notice: Subject to any disclaimer, the term of this patent is extended or adjusted under 35 U.S.C. 154(b) by 0 days.

(21) Appl. No.: 13/503,614

(22) PCT Filed: Oct. 25, 2010

(86) PCT No.: PCT/DK2010/050283
§ 371 (c)(1),
(2), (4) Date: Apr. 23, 2012

(87) PCT Pub. No.: WO2011/047689
PCT Pub. Date: Apr. 28, 2011

(65) Prior Publication Data
US 2012/0219618 A1    Aug. 30, 2012

(30) Foreign Application Priority Data
Oct. 23, 2009   (DK) .................................. 2009 01150

(51) Int. Cl.
*A61K 9/127*    (2006.01)
(52) U.S. Cl.
CPC .......... *A61K 9/1272* (2013.01); *A61K 9/1271* (2013.01)
(58) Field of Classification Search
USPC ...................................................... 424/450
See application file for complete search history.

(56) References Cited

U.S. PATENT DOCUMENTS

| | | | |
|---|---|---|---|
| 5,094,854 A | 3/1992 | Ogawa et al. | |
| 5,858,397 A | 1/1999 | Lim et al. | |
| 6,027,726 A | 2/2000 | Ansell | |
| 2003/0026831 A1 | 2/2003 | Lakkaraju et al. | |
| 2003/0147945 A1 | 8/2003 | Tardi et al. | |
| 2003/0170297 A1 | 9/2003 | Jorgensen et al. | |
| 2004/0022842 A1 | 2/2004 | Eriguchi et al. | |
| 2005/0118250 A1 | 6/2005 | Tardi et al. | |
| 2007/0014845 A1 | 1/2007 | Zhang et al. | |
| 2007/0286898 A1 | 12/2007 | Takagi et al. | |
| 2008/0085295 A1 | 4/2008 | Melvik et al. | |
| 2009/0092663 A1* | 4/2009 | Ponzoni et al. | .............. 424/450 |

FOREIGN PATENT DOCUMENTS

| | | | |
|---|---|---|---|
| CN | 101 103 972 | | 1/2008 |
| EP | 1254143 | | 11/2002 |
| WO | WO-01-58910 | * | 8/2001 |
| WO | WO 01/76555 | | 10/2001 |
| WO | WO 01/76556 | | 10/2001 |
| WO | WO-2005/000266 A2 | | 1/2005 |
| WO | WO 2006/048017 | | 5/2006 |
| WO | WO 2007/107161 | | 9/2007 |
| WO | WO-2009-141450 | * | 11/2009 |

OTHER PUBLICATIONS

Andresen et al., "Advanced strategies in liposomal cancer therapy: Problems and prospects of active and tumor specific drug release", *Progress in Lipid Research* vol. 44, 2005, pp. 68-97.
Andresen et al., "Triggered Activation and Release of Liposomal Prodrugs and Drugs in Cancer Tissue by Secretory Phospholipase A2", *Current Drug Delivery* vol. 2, 2005, pp. 353-362.
International Search Report for PCT/DK2010/050283 dated Feb. 18, 2011, 4 pgs.
Murakami et al., "Cellular components that functionally interact with signaling phospholipase A(2)s," Biochim Biophys Acta. 1488(1-2):159-66 (2000).

* cited by examiner

*Primary Examiner* — Celeste A Roney
(74) *Attorney, Agent, or Firm* — Clark & Elbing LLP; Kristina Bicker-Brady

(57)    ABSTRACT

The present invention provides a composition comprising a sPLA2 hydrolysable liposome, an exterior solution, and an interior solution within the liposome, —wherein the concentration of osmolytes is higher in the interior solution than in the exterior solution. The composition improves storage stability of sPLA2 hydrolysable liposomes, in particular at when stored at 2-8 degrees Celsius. The liposome preferably encapsulates cisplatin. The invention also provides methods of preparing the composition of the invention.

12 Claims, 16 Drawing Sheets

Table 1: Actual experimental settings of factors and the responses

| Exp no. | Batch no | NaCl conc. (w/v%) | Sucrose concetration (w/v%) | Pressure (KPa) | Initial particle size (nm) | DOE% Day 0 | DOE% Day 56 | Leakage % Day0-56 |
|---|---|---|---|---|---|---|---|---|
| 1 | LPB0057 | 0.9 | 0 | 5000 | 82.7 | 86.0 | 71.5 | 14.5 |
| 2 | LPB0058 | 1.9 | 0 | 5000 | 86.5 | 90.1 | 78.4 | 11.7 |
| 3 | LPB0059 | 0.9 | 10 | 5000 | 93.9 | 87.0 | 78.0 | 9.1 |
| 4 | LPB0060 | 1.9 | 10 | 5000 | 88.1 | 91.5 | 84.9 | 6.6 |
| 5 | LPB0061 | 0.9 | 0 | 20000 | 67.0 | 85.1 | 74.8 | 10.2 |
| 6 | LPB0062 | 1.9 | 0 | 20000 | 65.7 | 86.8 | 77.2 | 9.6 |
| 7 | LPB0063 | 0.9 | 10 | 20000 | 76.9 | 83.9 | 76.1 | 7.8 |
| 8 | LPB0064 | 1.9 | 10 | 20000 | 67.3 | 86.4 | 80.4 | 6.0 |
| 9 | LPB0065 | 0.9 | 5 | 12500 | 71.9 | 84.8 | 75.4 | 9.4 |
| 10 | LPB0066 | 1.9 | 5 | 12500 | 75.5 | 89.3 | 81.2 | 8.1 |
| 11 | LPB0067 | 1.4 | 0 | 12500 | 70.8 | 87.6 | 74.4 | 13.2 |
| 12 | LPB0068 | 1.4 | 10 | 12500 | 80.8 | 88.5 | 80.8 | 7.7 |
| 13 | LPB0069 | 1.4 | 5 | 5000 | 97.4 | 89.6 | 79.5 | 10.1 |
| 14 | LPB0070 | 1.4 | 5 | 20000 | 65.5 | 85.4 | 75.8 | 9.6 |
| 15 | LPB0071 | 1.4 | 5 | 12500 | 76.8 | 87.7 | 77.7 | 10.0 |
| 16 | LPB0072 | 1.4 | 5 | 12500 | 76.4 | 88.1 | 79.4 | 8.6 |
| 17 | LPB0073 | 1.4 | 5 | 12500 | 67.4 | 86.3 | 73.6 | 12.7 |

Figure 13

Table 2. Regression coefficients and significance (P) values of the model after back ward elimination

| Terms | Initial particle size | | Initial DOE% | | DOE% 56days | | Leakage (%) | |
|---|---|---|---|---|---|---|---|---|
| | Regression coefficient | P | Regression coefficient | P | Regression coefficient | P | Regression coefficient | P |
| Constant | 74.2 | $7.71*10^{-16}$ | 87.3 | $2.79*10^{-30}$ | 77.6 | $2.12*10^{-22}$ | 10.3 | $1.78*10^{-11}$ |
| NaCl | 3.43 | $2.34*10^{-2}$ | 1.73 | $1.25*10^{-5}$ | 2.63 | $2.67*10^{-4}$ | -0.90 | $2.89*10^{-2}$ |
| Suc | | | - | | 2.39 | $5.85*10^{-4}$ | -2.19 | $5.51*10^{-5}$ |
| Pre | -10.62 | $2.40*10^{-6}$ | -1.66 | $1.95*10^{-5}$ | -0.80 | $1.48*10^{-1}$ | -0.87 | $3.31*10^{-2}$ |
| NaCl*NaCl | | | - | | - | | -0.97 | $1.12*10^{-1}$ |
| Suc*Suc | | | - | | - | | - | - |
| Pre*Pre | 4.87 | $3.59*10^{-2}$ | - | | - | | - | - |
| NaCl*Suc | - | | - | | - | | - | - |
| NaCl*Pre | - | | - | | - | | - | - |
| Suc*Pre | - | | - | | -1.06 | $9.08*10^{-2}$ | - | - |
| R2 | 0.852 | | 0.855 | | 0.816 | | 0.812 | |
| Q2 | 0.749 | | 0.778 | | 0.661 | | 0.657 | |

Figure 14

Table 3. Overview of liposomal cisplatin formulations prepared with varying osmotic gradient

| Batch No | Interior water phase | | Exterior water phase | | Osmotic gradient | Leaky? |
|---|---|---|---|---|---|---|
| | Composition[‡] | Osmolarity[Δ] | Composition[‡] | Osmolarity[Δ] | Interior-Exterior | Yes/No[†] |
| LPB0021 | 8mg/mL Cis 0.9 wt% NaCl | 313 mOsm | 10 wt% Suc 10mM Phos | 317 mOsm | – 4 mOsm | Yes |
| LPB0022 | 8mg/mL Cis 1.0 wt% NaCl | 345 mOsm | 10 wt% Suc 10mM Phos | 317 mOsm | + 28 mOsm | Yes |
| LPB0023 | 8mg/mL Cis 0.9 wt% NaCl | 313 mOsm | 0.9 wt% NaCl | 286 mOsm | + 27 mOsm | Yes |
| LPB0024 | 8mg/mL Cis 1.1 wt% NaCl | 377 mOsm | 10 wt% Suc 10mM Phos | 317 mOsm | + 59 mOsm | Yes |
| LPB0025 | 8mg/mL Cis 1.2 wt% NaCl | 409 mOsm | 10 wt% Suc 10mM Phos | 317 mOsm | + 91 mOsm | Yes |
| LPB0026 | 8mg/mL Cis 1.8 wt% NaCl | 600 mOsm | 10 wt% Suc 10mM Phos | 317 mOsm | + 282 mOsm | No |
| LPB0027 | 8mg/mL Cis 0.9 wt% NaCl 10 wt% Suc | 611 mOsm | 10 wt% Suc 10mM Phos | 317 mOsm | + 294 mOsm | No |
| LPB0110 | 8mg/mL Cis 0.9 wt% NaCl 10 wt% Suc | 611 mOsm | 0.9 wt% NaCl 10mM Phos | 306 mOsm | + 306 mOsm | No |
| LPB0111 | 8mg/mL Cis 0.9 wt% NaCl 10 wt% Suc | 611 mOsm | 5 wt% Suc 0.45 wt% NaCl | 292 mOsm | + 319 mOsm | No |

[‡] Abbreviations: Cis = cisplatin, Suc = Sucrose, Phos = Sodium phosphate, NaCl = sodium chloride
[Δ] Assumes: 1) All material in solution,
2) Negligible increases in interior volumes upon dialysis, and
3) Use of available osmotic coefficients, otherwise assumed to be 1 corresponding to ideality.
[†] Definitions: Yes = More than (>) 10 % relative platinum leakage after 150 days of storage.
No = Less or equal (≤) 10 % relative platinum leakage after 150 days of storage.

Figure 15

Table 4. Overview of different liposomal drug formulations prepared with varying molecular weight

| | Liposomal oxaliplatin | Liposomal MTX | Liposomal bleomycin | Liposomal 5FU |
|---|---|---|---|---|
| Active substance | Oxaliplatin | Methrotraxate | Bleomycin | 5FU |
| Hydration media (Interior) | 15 mg/ml Oxaliplatin /10% sucrose /1mM calcium gluconate | 40mg/mL MTX/10mM Na-Phosphate | 25mg/mL Bleomycin /10% sucrose | 30mg/mL 5-FU/ 0.9%NaCl |
| Dialysis solution (Exterior) | 10% sucrose / 1mM calcium gluconate | 10% sucrose / 10mM Na-Phosphate | 10% sucrose / 1mM Calcium gluconate | 10% sucrose /10mM NA-Phospate |
| Interior osmolarity (mOsm) | 338 | 270 | 315 | 517 |
| Interior osmolarity (mOsm) | 300 | 317 | 3300 | 317 |
| Osmotic gradient (mOsm) | 38 | -47 | 15 | 200 |
| Molecular weight active substance (g/mol) | 397 | 454 | 1516 | 130 |
| Leakage (>10%) | No | No | No | Yes |

Figure 16

SPLA2 HYDROLYSABLE LIPOSOMES WITH IMPROVED STORAGE STABILITY

This application is a National Stage Application of PCT/DK2010/050283, filed 25 Oct. 2010, which claims benefit of Ser. No. PA 2009 01150, filed 23 Oct. 2009 in Denmark and which applications are incorporated herein by reference. To the extent appropriate, a claim of priority is made to each of the above disclosed applications.

FIELD OF THE INVENTION

The present invention relates to sPLA2 hydrolysable liposomal drug delivery systems with improved storage stability, in particular improved storage stability at 2-8 degrees Celsius.

BACKGROUND

Liposomes for Drug Delivery

Liposomes are microscopic spheres which were developed as drug delivery vehicles/systems in the 1980s. The first liposome-based pharmaceuticals were approved for commercial use in the 1990s.

Liposomes have three distinct compartments that can be used to carry various compounds such as drugs: The interior aqueous compartment; the hydrophobic bilayer; and the polar inter-phase of the inner and outer leaflet. Depending on the chemical nature of the compound to be encapsulated it will be localised to either of the compartments.

Currently, there are several parenteral liposome-drug formulations available on the market. Water soluble drugs tend to be localised in the aqueous compartment of liposomes, and examples of drugs encapsulated in liposome's are, e.g. doxorubicin (Doxil), doxorubicin (Myocet) and daunorubicin (DaunoXone). Examples of drugs intercalated in the liposome membrane are, e.g. amphotericin B (AmBisome), amphotericin (Albelcet B), benzoporphyrin (Visudyne) and muramyltripeptide-phosphatidylethanolamine (Junovan).

Liposomes are considered a promising drug delivery system since they passively target tumor tissue by using the pathophysiological characteristics of solid tumors such as hyperplasia and increased vascular permeability but also a defect in lymphatic drainage. These features facilitate extravasation of nanoparticles and the liposomes can be retained in the tissue for longer time due to the enhanced permeability and retention effect (EPR).

The property of liposomes as drug delivery vehicles is crucially dependent on their surface charge, permeability, solubility, stability etc. which is significantly influenced by the lipids comprised in the liposome composition. In addition, the drug to be encapsulated in the liposome may need further requirements to be considered in preparing a stable liposome formulation.

Considerations regarding safety and drug efficacy require that liposome formulations maintain their properties, i.e. remain stable, from the time of preparation until administration.

Furthermore, it is desirable that such formulations are intact during the transport in the treated subject until they reach the target site where the drug is specifically released.

Various targeting strategies for liposomes have been described, e.g. conjugation to cell specific ligands such as antibodies.

sPLA2 Hydrolysable Liposomes

Another approach has been suggested based upon elevated levels of secretory phospholipase A2 (sPLA2) in cancerous tissue and also at sites of inflammation. The basic idea is that liposomes can be prepared which are hydrolysable by sPLA2 and that hydrolysis by sPLA2 leads to release of the drug encapsulated within the liposome. Moreover, the products of sPLA2 hydrolysis, a lysolipid and a fatty acid act as permeabilizers of cell membranes leading to increased cell uptake of the drug. Since sPLA2 levels are elevated in cancerous tissues and at sites of inflammation, sPLA2 activated liposomes may be used to preferentially deliver encapsulated drugs to such sites.

Storage Stability of sPLA2 Hydrolysable Liposomes sPLA2 hydrolysable liposomes pose special challenges with regards to storage stability. These challenges are based in the particular lipid composition necessary for effective sPLA2 hydrolysis.

In general, many parameters influence storage stability, and it is difficult to predict the consequences of altering buffer composition on storage stability as this affects not only the osmolarity, but also the membrane stability.

PRIOR ART

A number of documents have described sPLA2 activated liposomes, and various documents have studied storage stability of liposomes. However, none of the documents have studied the particular storage problems posed by sPLA2 hydrolysable liposomes.

WO0158910 described sPLA2 activated liposomes comprising prodrugs of mono-ether lyso-phospholipids. This document also described encapsulation of additional bioactive compounds.

WO0176555 suggested the use of a lipid-based drug delivery system for treatment of diseases or conditions associated with a localized increase in extracellular sPLA2 in cutaneous or subcutaneous tissue of a mammal, for administration of a prodrug of an ether-lysolipid that is activated by sPLA2. The system further comprised a so-called edge active compound.

WO0176556 suggested the use of a lipid-based drug delivery system for treatment or prevention of a parasitic infection selected from Leishmaniasis, Tryponosomiasis, malaria, Entaboeba, Histolyticasis and "Oriental liver fluke chlomorchis sinensis", wherein the system comprised prodrugs in the form of lipid derivatives that are activated by sPLA2. The liposomes may contain an additional bioactive compound.

WO06048017 and WO07107161 did also describe sPLA2 activated liposomes.

U.S. Pat. No. 5,094,854 disclosed temperature sensitive liposomes optimized with regards to stability and release by heating. The liposomes described in this document preferably has an interior solution with an osmotic pressure 1.2 to 2.5 times higher than that of body fluid of warm blooded animals and have a phase transition temperature of 40-45 degrees Celsius. The liposomes disclosed in this document are not substrates of sPLA2, because they do not have the appropriate lipid composition.

Most liposomal formulations do not have problems with leakage during storage. Rather the formulations are so stable that it is difficult to get a release of encapsulated compounds at the intended sites.

SUMMARY OF THE INVENTION

In a first aspect, the present invention provides a composition comprising
a sPLA2 hydrolysable liposome,
an exterior solution,
and an interior solution within the liposome,
wherein the concentration of osmolytes is higher in the interior solution than in the exterior solution.

The composition improves storage stability of sPLA2 hydrolysable liposomes, in particular when stored at 2-8 degrees Celsius. The liposome preferably encapsulates cisplatin.

The invention also provides methods of preparing the composition of the invention.

BRIEF DESCRIPTION OF THE FIGURES

FIG. 13.
Table 1 showing actual experimental settings of factors and the responses.

FIG. 14.
Table 2 showing regression coefficients and significance (P) values of the model after back ward elimination.

FIG. 15.
Table 3 showing overview of liposomal cisplatin formulations prepared with varying osmotic gradient.

FIG. 16.
Table 4 showing overview of different liposomal drug formulations prepared with varying molecular weight.

DISCLOSURE OF THE INVENTION

Figure 1:
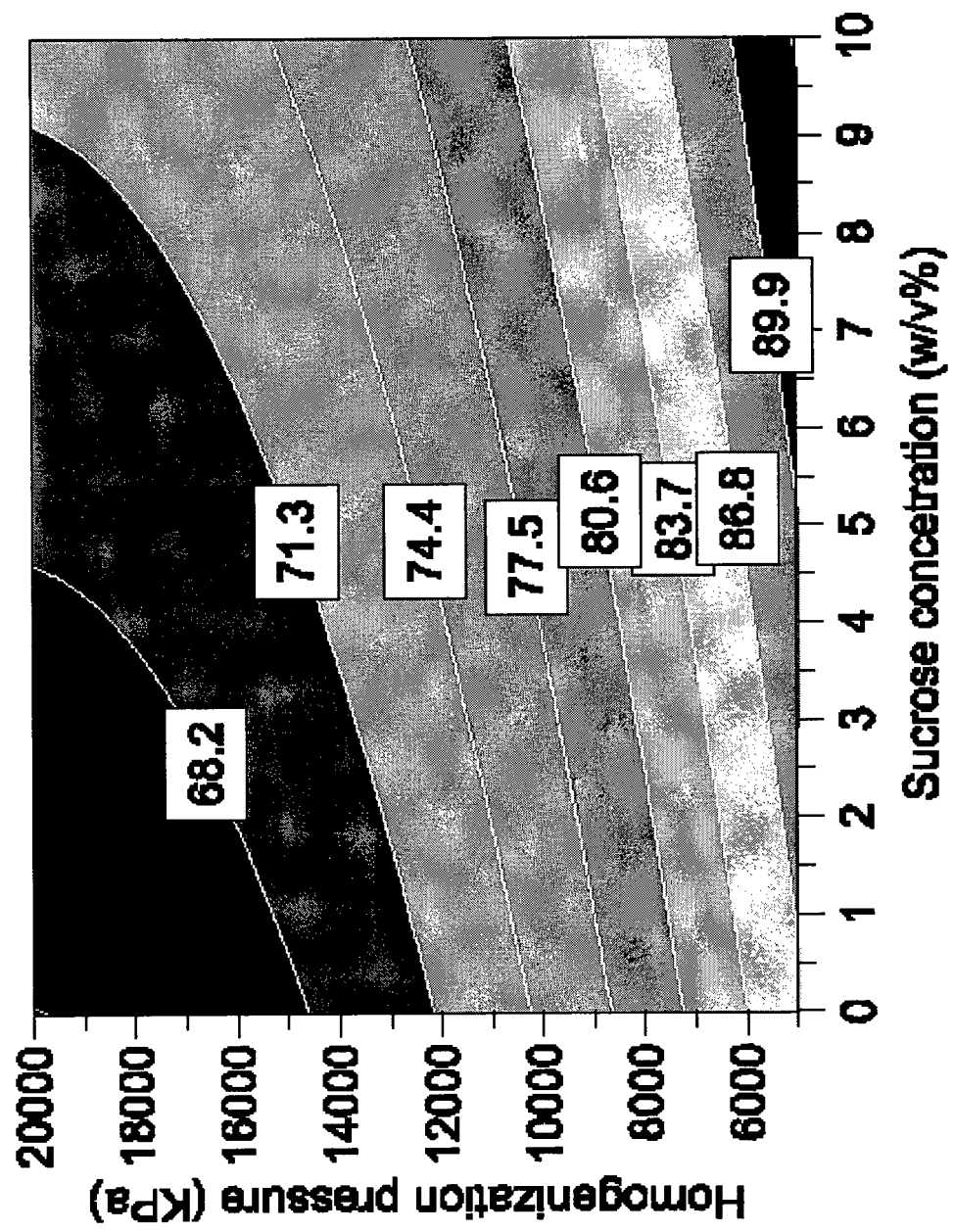
FIG. 1.
Contour plot illustrating the influence of sucrose concentration and homogenization pressure used during liposome preparation on particle size. Numbers inside the contour plot indicate particle size FIG. 2.
Total Pt concentrations in liposomes as a function of particle size.

The present invention is based on the discovery that leakage from sPLA2 hydrolysable liposomes may be reduced by storage in an exterior solution that has a lower concentration of osmolytes than the interior solution of the liposome.

The leakage problem was observed in relation to storage of cisplatin encapsulated in sPLA2 hydrolysable liposomes to be used for a phase 1 study of an iso-osmotic formulation of cisplatin encapsulated in sPLA2 hydrolysable liposomes. In this formulation, the interior solution was 0.9% NaCl and the exterior solution was 10 mM phosphate buffer at pH 6.5, 1 mM NaCl and 10% sucrose. Because of a high degree of leakage when stored 2-8 degrees Celsius, the iso-osmotic formulation had to be stored at minus 80 degrees Celsius, which is not an optimal solution for a commercial product. Thus, not all hospitals have facilities for storage at minus 80 degrees. Moreover, transportation at minus 80 degrees Celsius is cumbersome.

Additionally, when thawing the vials before use, problems with breakage of the vials were encountered and thawing caused significant leakage from the liposomes.

As mentioned, it is believed that the leakage problem is a consequence of the specific requirements with regards to lipid composition of the sPLA2 hydrolysable liposomes. In particular it is believed that the leakage is caused by the absence of or low amounts of stabilizing agents such as cholesterol in sPLA2 hydrolysable liposomes. Moreover, the anionic nature of sPLA2 hydrolysable liposomes may influence leakage.

Thus, there is a need for a composition comprising sPLA2 hydrolysable liposomes with reduced leakage when stored at 2-8 degrees Celsius.

The terms "reduced leakage" and "improved stability" with respect to sPLA2 liposomes are used interchangeably herein. As will be understood, leakage is related to and may be described by changes in the concentration (or amount) of a therapeutic agent in the interior solution, preferably over time.

In a first aspect, the present invention provides a composition comprising
a sPLA2 hydrolysable liposome,
an exterior solution,
and an interior solution within the liposome,
wherein the concentration of osmolytes in the interior solution is higher than the concentration of osmolytes in the exterior solution.

The composition will normally be a pharmaceutical composition.

In a preferred embodiment, the liposome comprises a therapeutic agent encapsulated within the liposome. The therapeutic agent is typically dissolved in the interior solution. However, the therapeutic agent may also be partly or fully precipitated, e.g. due to reduced solubility during storage as compared to the solubility during encapsulation.

The solubility during encapsulation may be higher because of a higher temperature.

It is preferred that the therapeutic agent has a molecular weight of less than 350 g/mol, since the leakage problem typically occurs for smaller agents and it is believed that smaller agents can more easily pass the lipid bilayer of the liposome.

It is even more preferred that the therapeutic agent is cisplatin (cis-diamminedichloroplatinum(II)). As mentioned above, sPLA2 hydrolysable liposomes encapsulating cisplatin tend to leak during storage.

In a preferred embodiment, the only therapeutic agent in sPLA2 hydrolysable liposome is cisplatin. Thus, the interior solution only comprises osmolytes and cisplatin and optionally a buffer.

Chloride ions prevent cisplatin from forming an undesired highly toxic hydration product. Therefore, it is preferred that the interior solution comprises NaCl or KCl at a concentration of at least 0.2% or 0.4%, more preferably 0.2-2.5% w/w, or 0.4-1.8% and most preferably between 0.8-1%. In some embodiments, other chloride salts may be used. NaCl normally is preferred over KCl.

In some embodiments, it is preferred that the exterior solution comprises NaCl or KCl at a concentration of at least 0.2% or 0.4%, more preferably 0.2-2.5% w/w, or 0.4-1.8% and most preferably between 0.8-1%. The typical concentration is 0.9%. Thus, if minor amounts of cisplatin leaks out of the liposome, the presence of chloride ions will minimize the formation of toxic hydration products. Again, NaCl is normally preferred over KCl.

In one embodiment, there are no divalent cations, such as Calcium ions, in the exterior solution.

In another embodiment, divalent cations may be included in the exterior solution. The interior solution does typically not include a buffer. Moreover, sulfates are not normally included in the interior solution.

In one embodiment of the composition, the interior solution comprises at least 1.4% NaCl or KCl and more preferably 1.8% NaCl or KCl and does not comprise a viscosity enhancer, preferably selected from the group consisting of sugars such as lactose, sucrose, maltose, galactose, glucose and hydrophilic polymers such as starch, dextran, polyvinyl alcohol, polyvinyl-pyrrolidone, dextrin, xanthan and partly hydrolyzed cellulose oligomers and proteins and polypeptides.

In another embodiment of the composition, the interior solution comprises at least 5% of a viscosity enhancer. Preferably, the viscosity enhancer is selected from the group consisting of sugars such as lactose, sucrose, maltose, galactose, glucose and hydrophilic polymers like starch, dextran, polyvinyl alcohol, polyvinyl-pyrrolidone, dextrin, xanthan and partly hydrolyzed cellulose oligomers and proteins and polypeptides. It should be recognized that viscosity enhancers will also function as osmolytes.

When the interior solution comprises a viscosity enhancer, it is preferred that the concentration is more than 5% w/w. Even more preferred is a concentration of more than 6, 7, 8, 9 or 10% %. In a preferred embodiment, the viscosity enhancer selected from the group consisting of sugars such as lactose, sucrose, maltose, galactose, glucose and hydrophilic polymers like starch, dextran, polyvinyl alcohol, polyvinyl-pyrrolidone, dextrin, xanthan and partly hydrolyzed cellulose oligomers and proteins and polypeptides. Most preferred are sugars, in particular sucrose.

In general, it is preferred that the exterior solution has an osmolyte concentration around 300 mM since this is the physiological osmolyte concentration. Thus, in embodiment, it is preferred that the exterior solution has an osmolyte concentration between 200 and 400 mM, more preferably between 250-350 mM and most preferred between 275 and 325 mM.

The composition of the invention is characterized in that there is a difference in osmolyte concentration between the interior and the exterior solution. The difference is herein also termed the osmotic gradient.

As demonstrated in the examples section, an osmotic gradient (exterior concentration of osmolyte subtracted from the interior concentration of osmolyte) of 27 mM cannot reduce leakage sufficiently. A gradient of 59 mM reduces leakage further as do also a gradient of 91 mM. It should be noted that the osmolyte concentration is the total concentration of all solute particles, which is often referred to as the osmolarity (Osm) of a solution.

In one embodiment, the osmolarity of the solutions are corrected using the osmotic coefficients of the solute particles.

It is preferred that the osmotic gradient should be more than 27 mM. More preferred is an osmotic gradient of more than 59 mM or more than 91 mM. Even more preferred is more than 100 mM, such as more than 150 mM, more than 200 mM, more than 250 mM, more than 275 mM and more than 300 mM.

In one embodiment, the concentration of osmolytes in the interior solution is assumed to be the same as the concentration of the osmolytes in the hydration solvent used when preparing the liposomes. I.e. when reference is made to the osmolyte concentration in the interior solution, this concentration can easily be determined since it is the concentration of osmolytes in the hydration solvent.

The actual concentration of osmolytes in the interior solution may not be identical to the concentration of osmolytes in the hydration solvent, because water may move into the liposome after formation and hence decrease the concentration of osmolytes (while increasing the osmotic pressure within the liposome)

The maximal osmotic gradient is preferably 1500 mM, more preferably 1200 mM and most preferably 900 mM. If the osmotic gradient too high, it is believed that the liposomes will initially be leaky, such that osmolytes will pass the membrane until a maximal tolerable gradient is established, where after leakage will be at a minimum.

Thus, the osmotic gradient is typically between 27 and 900 mM, more preferably between 200 and 600 mM and most preferably between 280 and 320 mM.

The pH of the exterior solution typically has a pH between 5 and 7 and the interior solution typically has a pH between 5 and 7. Appropriate buffers may be used to keep the pH at the desired value.

However, in one embodiment, the interior solution and/or the exterior solution do not comprise a buffer, preferably phosphate buffer. In some embodiments, phosphate buffers are undesired, because they promote conversion of cisplatin to byproducts.

Particular preferred compositions where cisplatin is encapsulated in the liposome comprise the following:

1) Interior solution: 0.8-1.0% NaCl, such as 0.9% NaCl and 9-11% sucrose, such as 10% sucrose.

Exterior solution: 8-12 mM Phosphate buffer (pH6.5), such as 10 mM Phosphate buffer (pH6.5)+9-11 sucrose %, such as 10% sucrose.

2) Interior solution: 1.6-2.0% NaCl, such as 1.8% NaCl
   Exterior solution: 8-12 mM Phosphate buffer (pH6.5), such as 10 mM Phosphate buffer (pH6.5)+9-11% sucrose, such as 10% sucrose.
3) Interior solution: 0.8-1.0% NaCl, such as 0.9% NaCl and 9-11% sucrose, such as 10% sucrose.
   Exterior solution: 8-12 mM Phosphate buffer (pH6.5), such as 10 mM Phosphate buffer (pH6.5)+0.35% - 0.55% such as 0.45% NaCl+4-6% sucrose, such as 5% sucrose.
4) Interior solution: 1.6-2.0% NaCl, such as 1.8% NaCl
   Exterior solution: 8-12 mM Phosphate buffer (pH6.5), such as 10 mM Phosphate buffer (pH 6.5)+0.8-1.0% NaCl, such as 0.9% NaCl.

The concentration of the therapeutic agent in the final composition is typically between 0.1 mg/ml to 15 mg/ml. When the therapeutic agent is cisplatin, it is preferred that the concentration is between 0.5 mg/ml and 1.5 mg/ml. Such concentrations can be achieved by using a cisplatin concentration of 8 mg/ml in the hydration solution during liposome preparation. A concentration of 8 mg/ml can be achieved by heating the hydration solution to a temperature of 65% degrees Celsius.

The liposomes of the composition preferably have an average size (diameter) between 50 and 200 nm, more preferably between 75 and 160 nm.

The liposomes of the composition should have a leakage of less than 20%, 15% or 10%, more preferably less than 9%, 8% or 7% leakage after 56 days of storage at a temperature between 2 and 8 degrees Celsius. As demonstrated in the examples section, this can be achieved by adjusted the osmotic gradient.

When referring to the percentage of leakage, reference is to the amount of cisplatin in the liposomes after a step of dialysis or ultrafiltration compared to the amount of cisplatin in the liposomes after storage. After a step of dialysis or ultrafiltration, the exterior solution may comprise 5% of the total amount of cisplatin in the composition. Thus, the internal solution comprises 95% of the cisplatin in the composition. After storage, the internal solution may comprise 85.5% of the total amount of cisplatin and the exterior solution consequently 14.5%. The leakage has then been 9.5/95=10%.

In a preferred embodiment, the composition of the first aspect is prepared by the method of the second aspect.

sPLA2 Hydrolysable Liposomes sPLA2 hydrolysable liposomes for use in the composition of the present invention are defined in more detail in the following embodiments. In its broadest embodiment, the term sPLA2 hydrolysable liposomes refer to liposomes that are hydrolysable under physiological conditions, particular in cancerous tissue.

Preferably, the sPLA2 hydrolysable liposomes comprises between 20% and 45% (mol/mol) of an anionic lipid. The content of anionic lipid affects important characteristics of the liposome, such as the rate of sPLA2 mediated lipid hydrolysis of the liposome and also the immune response toward the liposome.

As the content of anionic lipid increases, so does the rate of lipid hydrolysis by $sPLA_2$ (and the release of drug). It has been demonstrated that a reasonable rate of hydrolysis can be achieved by anionic lipid content between 20% and 45%. Thus, in one embodiment, the content of anionic lipid is at least 20%. In another embodiment, the content of anionic lipid is no more than 45%. In yet another embodiment, the anionic lipid content of the liposome is selected from the group consisting of between 20% and 45%, between 25% and 45%, between 28% and 42%, between 30% and 40%, between 32% and 38% and between 34% and 36%.

As mentioned, also the immune response toward the liposomes is affected by the content of anionic lipid. Thus, the clearance rate of the liposome in body may be reduced by keeping the content of the anionic lipid in the liposome below a certain level and the present inventors have recognized that the content of anionic lipid in the liposome can be used to strike a balance between hydrolysis rate of $sPLA_2$ and clearance by the reticuloendothelial system.

Preferably the anionic lipid is a phospholipid and preferably, the phospholipid is selected from the group consisting of PI (phosphatidyl inositol), PS (phosphatidyl serine), DPG (bisphosphatidyl glycerol), PA (phosphatidic acid), PEOH (phosphatidyl alcohol), and PG (phosphatidyl glycerol). More preferably, the anionic phospholipid is PG. Preferably, the lipids comprise stearoyl chains. Thus preferably PG is DSPG etc.

Hydrophilic Polymers

In a preferred embodiment, the sPLA2 hydrolysable liposome for use in the present invention further comprises a hydrophilic polymer selected from the group consisting of PEG [poly(ethylene glycol)], PAcM [poly(N-acryloylmorpholine)], PVP [poly(vinylpyrrolidone)], PLA [poly(lactide)], PG [poly(glycolide)], POZO [poly(2-methyl-2-oxazoline)], PVA [poly(vinyl alcohol)], HPMC (hydroxypropylmethylcellulose), PEO [poly(ethylene oxide)], chitosan [poly(D-glucosamine)], PAA [poly(aminoacid)], poly-HEMA [Poly(2-hydroxyethylmethacrylate)] and co-polymers thereof.

Most preferably the polymer is PEG with a molecular weight between 100 Da and 10 kDa. Particular preferred are PEG sizes of 2-5 kDa (PEG2000 to PEG5000), and most preferred is PEG2000.

The inclusion of polymers on liposomes is well known to the skilled artisan and can be used to increase the half-life of the liposomes in the bloodstream, presumably by reducing clearance by the reticuloendothelial system.

Preferably, the polymer is conjugated to the head group of phospatidyl ethanolamine. Another option is conjugation to ceramide (even though this lipid is not hydrolyzable by $sPLA_2$). When the polymer is conjugated to phospatidyl ethanolamine, a negative charge is introduced and hence DSPE-PEG is regarded as an anionic lipid (contrary to DSPE which is regarded as a neutral lipid).

The polymer-conjugated lipid is preferably present at an amount of at least 2%. More preferably, the amount is at least 5% and no more than 15%. Even more preferably, the amount of polymer-conjugated lipid is at least 3% and no more than 6%. Liposomes containing anionic phospholipids and ≤2.5% DSPE-PEG2000 have increased tendency to aggregate in the presence of calcium. This can usually be observed by formation of high viscous gel. Liposomes containing anionic phospholipids and >7.5% DSPE-PEG2000 causes the liposomes to sediment or phase separate.

Neutrally charged lipid components in the liposome

Preferably, the liposome to be used in the present invention also comprises an uncharged phospholipid selected from the group consisting of zwitterionic phospholipids comprising PC (phosphatidyl choline) and PE (phosphatidylethanolamine). Most preferably, the zwitterionic phospholipid is PC.

In contrast to anionic phospholipid, zwitterionic phospholipid serves as a charge neutral $sPLA_2$-hydrolyzable lipid component in the liposome. By combining zwitterionic- and anionic phospholipid in the same liposome, it is possible to adjust to a desired surface charge density which complies with both sufficiently high sPLA$_2$ hydrolysis and a low clearance rate in the blood.

The amount of zwitterionic phospholipid in the liposome is preferably between 40% and 75% and more preferably between 50 and 70%.

Preferably, the lipids (anionic lipids, neutral lipids and polymer conjugated lipids) comprise stearoyl chains). Thus preferably PG is DSPG, PE is preferably DSPE etc.

Ether-Phospholipids

Some or all of the phospholipids may be ether-phospholipids.

Thus, they may harbour an ether-bond instead of an ester-bond at the sn-1 position of the glycerol backbone of the phospholipid. When sPLA$_2$ hydrolyze this particular type of phospholipids, mono-ether lyso-phospholipids are produced and these are toxic to e.g. cancer cells. I.e. ether phospholipids may be seen as pro-drugs of mono-ether lyso-phospholipids and liposomes of the invention can be used to deliver such pro-drugs to the sPLA$_2$-enhanced environment of cancer cells, where the pro-drugs are activated by sPLA$_2$ hydrolysis. Ether-phospholipids have been described in EP 1254143 and WO 2006/048017, the contents of which are hereby incorporated by reference.

In one embodiment, the sPLA2 activated liposomes as used in the present invention does not comprise ether-phospolipids.

Other Pro-Drugs

The moiety released from the lipid by sPLA$_2$ to create a lysolipid may also be a drug. Thus, a liposome may comprise pro-drugs of mono-ether lysolipids, pro-drugs released from the lipid by sPLA$_2$ and other therapeutic agents, as further outlined below.

In one embodiment, the sPLA2 activated liposomes as used in the present invention does not comprise prodrugs released from the lipid by sPLA2.

Stabilizing Agent

The liposome may also be stabilized by the inclusion of cholesterol as membrane component in the liposome. However, high amounts of cholesterol in the liposome have a negative effect on hydrolysis by PLA$_2$ and therefore it is preferred that the liposome comprises no more than 10% cholesterol. Even more preferably, the liposome comprises less than 1% cholesterol, less than 0.1% or does not comprise any cholesterol at all.

The alkyl chain length of the lipids comprising the liposome may be adjusted for optimal PLA$_2$ hydrolysis rate and minimum leakage of entrapped compound out of the liposome. Preferably, the alkyl chains are C18 or C16 saturated chains.

As described above, the liposomes may comprise pro-drugs of mono-ether lyso-lipids and/or of the moiety released from the lipid by sPLA$_2$ to create the lysolipid.

Physical-Chemical Characteristics of the Liposomes

The liposome can be unilamellar or multilamellar. Most preferably, the liposome is unilamellar. The diameter of the liposome should be between 50 and 400 nm, preferably between 80 and 160 nm and most preferable between 90 and 120 nm.

Preferably, the Poly Dispersity Index (PDI) of the liposomal formulation of the second aspect of the invention should not exceed 0.2 and more preferable is 0.10 or less. A PDI value in this range expresses a relatively narrow particle size-distribution in the formulation.

As will be clear from the above, it is preferred that at least one of the lipids comprising the liposome is a substrate for sPLA$_2$ when present in the liposome.

In one embodiment, the liposome comprises lipids which are hydrolysed by sPLA$_2$ at the sn-3 position instead of at the sn-2 position. Such unnatural lipids and liposomes comprising unnatural lipids have been disclosed in WO 2006/048017, the content of which is hereby incorporated by reference.

In a most preferred embodiment, the liposomes to be used in the present invention comprise 70% DSPC, 25% DSPG and 5% DSPE-PEG.

Method of Preparation

A second aspect of the invention is a method comprising the steps a) Preparing a lipid mixture by dissolving selected lipids in an organic solvent b) Hydrating the product of step a) with an aqueous hydration solvent so as to form liposomes c) Removing the organic solvent of step a) either before addition of the aqueous hydration solvent or after the addition of the aqueous hydration solvent d) exchanging the hydration solvent with an exterior solution, which has a lower osmolyte concentration than the hydration solution e) Thereby forming a composition as described in the first aspect of the invention.

The hydration solvent may be exchanged by centrifugation, ultrafiltration, dialysis or similar. After changing the hydration solvent to the exterior solution, it is preferred that less than 15%, less 10% or more preferably less than 8% or 6% of therapeutic agent is present in the exterior solution.

Preferably, the degree of drug encapsulation in the liposomes should be >70%, more preferably >95% and most preferably >99%. The degree of drug encapsulation is the ratio of drug encapsulated to the total amount of drug in the formulation.

Preferably, the organic solvent is removed before addition of hydration solvent.

The method may further comprise high sheer mixing to reduce the size of the liposomes.

The method may further comprise a step of extruding the liposomes produced in step c) through a filter to produce liposomes of a certain mean size.

The method may also comprise a step of sonicating the liposomal formulation to produce liposomes of a certain size.

The method may also comprise homogenization at a pressure between 5000 and 20000 KPa.

Preferably, the liposome is a liposome as described in the first aspect of the invention, i.e. lipids are selected accordingly.

Liposomes may be loaded with at least one therapeutic agent by solubilizing the drug in the organic solvent or hydration solvent used to prepare the liposomes. Preferably, the therapeutic agent is solubilised in the hydration solvent and the therapeutic agent is preferably cisplatin.

Alternatively, ionisable therapeutic agent can be loaded into liposomes by first forming the liposomes, establishing an electrochemical potential, e.g. by way of a pH gradient, across the outermost liposome layer, and then adding the ionisable therapeutic agent to the aqueous medium external to the liposome.

EXAMPLES

Example 1

Optimization of Storage Stability of sPLA2 Hydrolysable Liposomes

Abstract

It has been observed that upon storage at 2-8° C. LiPlaCis (liposomal cisplatin) may have up to 30% leakage during the first couple of months. Leakage is most extensive during the first two months, and beyond this period only minor leakage occurs.

A factorial design was set up to test stability of LiPlacis at 2-8° C. Formulations were prepared with varying interior buffer composition, and homogenized at different pressures according to composite face design. 3 factors were tested at 3 levels:

Interior NaCl concentration (0.9, 1.4, and 1.9%)
Interior Sucrose concentration (0.5, and 10%)
Homogenization pressure used during preparation (5000, 12500, and 20000 KPa).

Leakage from formulation was demonstrated to be influenced by all parameters tested. Increasing the sucrose and NaCl concentration on liposome interior and having low homogenization pressure during liposome preparation results in higher drug retention during storage. The formulations having the highest degree of encapsulation after two months of storage was prepared with 1.9% NaCl and 10% sucrose on the liposome interior, and homogenized at 5000 KPa. No significant changes were seen on particle size during storage for any of the formulations prepared.

Materials and Methods

Preparation of sPLA2 liposomes (LiPlaCis)

1,2-di(octadecanoyl)-sn-glycero-3-phosphocholine (DSPC), 1,2-di(octadecanoyl)-sn-glycero-3-phosphoglycerol (DSPG), and 1,2-di(octadecanoyl)phosphatidylethanolamine-methoxy poly (ethylene glycol) 2000 (DSPE-PEG 2000) were all purchased from Lipoid (Ludvigshafen, Germany). Sucrose was purchased from Sigma-Aldrich (St. Louis, Mo.). Sodium chloride and sodium dihydrogen phosphate were purchased from Merck (Darmstadt, Germany) and J. T. Baker (Deventer, Holland), respectively. Iridium atomic absorption standard solution was purchased from Sigma-Aldrich (St. Louis, Mo.). Slide-A-Lyzer 10K MWCO dialysis casttes were purchased from Thermo Scientific (Rockford, Ill.). Amicon® Ultra-4 Ultracel-30k centrifuge filter devices were purchased from Millipore (Bedford, Mass.).

Preparation of LiPlaCis

Homogeneous lipid mixture (DSPC/DSPG/DSPE-PEG2000 70:25:5 mol-%) was prepared by dissolving lipids in chloroform/methanol 9:1 (v/v). The solvent was evaporated from the lipid mixtures at a temperature of 50oC, using a gentle stream of nitrogen gas. Residual solvent was evaporated by storing under vacuum overnight in a Christ Epsilon 2-4 freeze-dryer from Martin Christ Freeze Dryers GmbH (Harz, Germany). Multilamellar vesicles (MLVs) were prepared, by dispersing the lipid films in a 65 oC hot hydration media containing 8 mg/mL cisplatin and varying concentrations of sucrose and sodium chloride according to table 1. The lipids were hydrated for ½ h at 65 oC. During hydration samples were vortexed each 5 min. Hydrated lipid suspension was homogenized in EmulsiFlex-C3 from Avestin, Inc. (Ontartio, Canada) at varying pressure (5000-20,000 KPa) according to table 1. All steps of homogenization were carried out at a temperature of 65° C. Unentrapped cisplatin was removed from the formulation by precipitation and dialysis. Precipitation was carried out in two steps; first at 25° C. for 1 h, and then at 5 ° C. for 1 h. Dialyzed against 100x volume 2 times in 10 mM Phosphate buffer containing 10% sucrose pH 6.5 for 18 and 24h, respectively. Immediately after preparation the formulations were divided into glass vials with 500 μl sample in each vial. Vials were sealed with cap and placed in a refrigerator (2-8° C.). The day of placement in refrigerator is considered as the initiation date. Samples are taken continually during storage, and analyzed by ICP-MS and Zetasizer nano for determination of Pt concentrations and particle size, respectively.

Determination of Particle Sizes

Two drops of LiPlaCis was mixed into 10 mL Milli-Q water. 1 mL mixture was transferred into a disposable cuvette and particle size was measured on Zetasizer Nano ZS Dynamic Light Scattering device from Malvern Inc. (Worcestershire, United Kingdom). Particle sizes were determined three times at a temperature of 25 oC using water as the internal reference substance. A mean Z-average particle size (i.e. diameter) was calculated based on the three measurements.

Determination of Degree of Encapsulation

The liposomes were diluted by a factor 100 in dialysis solution. Subsequently, the diluted liposomes were equilibrated for 1 h at 25 oC. Part of the diluted liposomes was then centrifuged at 2500 g for 30 min. at 15 oC in an Amicon® Ultra centrifugal filter devices (30K MWCO) from Millipore (Billerica, Mass.). Samples before centrifugation (i.e. 100 times diluted liposomes) and after centrifugation (permeate) were diluted 100 fold in Milli-Q water. 1 vol. % iridium atomic absorption standard solution (1.05 ppm) was added to all samples as internal standard. A Perkin-Elmer PESCIEX Elan 6000 inductively coupled plasma device (Ontario, Canada) equipped with a cross flow nebuliser and pt conus was used for measuring platinum levels in samples of LiPlaCis.

Experimental Design and Statistical Analysis

Experiment was conducted using a central composite face design to investigate the linear, quadratic, and cross product effects of three factors, each varied at three levels and also includes three center points for replication. Factors and their levels are shown in table 1. The three factors chosen were interior NaCl concentration (w/v %), interior sucrose concentration (w/v %), and homogenization pressure (KPa).

The design of the experiment employed is presented in table 1. A software package (Modde 8.0, Umetri, Umeå., Sweden) was used to fit the second order model to the independent variables.

The response surface model was fitted to the following equation:

$$Y = \beta_o + \sum_{i=1}^{n} \beta_i X_i + \sum_{i=1}^{n} \beta_{ii} X_i^2 + \sum_{i=1}^{n-1} \sum_{j=i+1}^{n} \beta_{ij} X_i X_j + \varepsilon$$

Where Y is the response variables, $X_i$ the ith independent variable, $\beta_o$ the intercept, $\beta_i$ the first-order model coefficient, $\beta_{ii}$ the quadric coefficient for variable i and flu $\beta_{ij}$ is the model coefficient for the interaction between factor i and j, $\varepsilon$ is the combination of the experimental error for the factors. The quadratic term make it possible to obtain information about curvatures in the response.

The coefficient of determination ($R^2$) and lack-of-fit test were used to determine whether the constructed model was adequate to describe the observed data. $R^2>0.8$ indicates that the model has acceptable qualities. Where it is possible, the model is simplified by dropping terms, which were not significant (P>0.05) by analysis of variance. Terms were however not removed from the model if $R^2$ become below 0.8.

RSM was used to evaluate the effect of selected factors on initial particle size, DOE % immediately after preparation, DOE % and leakage after 56d storage at 2-8° C., Results and Discussion Model Fitting The best-fitting models by multiple regression and backward elimination were determined. The observed and predicted values were sufficiently correlated. The statistics for model coefficients and probability (P) values for the response variables were calculated (Table 2). The models generated were generally satisfactory for the evaluations, as the observed and the predicted results were well correlated. According to analysis of variance there was no lack of fit for any of the generated model.

Particle Size

Data shows that the homogenization pressure has the most significant influence on the particle size. With a higher homogenization pressure used during preparation the particle size decrease. Sucrose concentration used during preparation was also demonstrated to have significant influence on the particle size. Increasing sucrose concentration results in a larger particle size. Contour plot illustrating the influence of interior sucrose concentration and homogenization pressure used during liposome preparation on particle is presented in FIG. 1.

Figure 2:
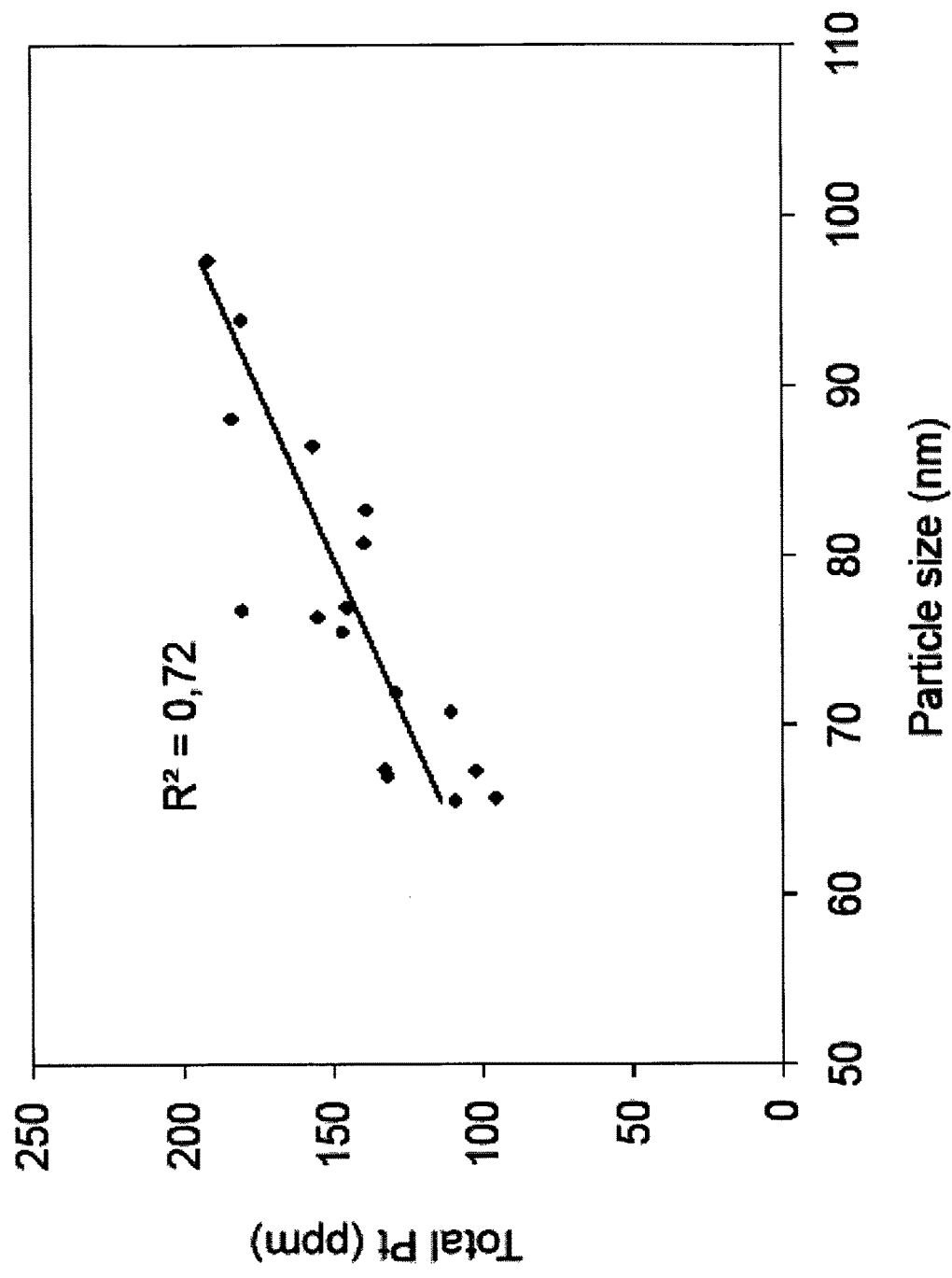

From FIG. 2 it can be seen that with larger particle size there is usually seen a higher amount of encapsulated cisplatin. With larger particle size it would also be expected that the interior volume would increase, allowing more Pt to be encapsulated.

Figure 3:
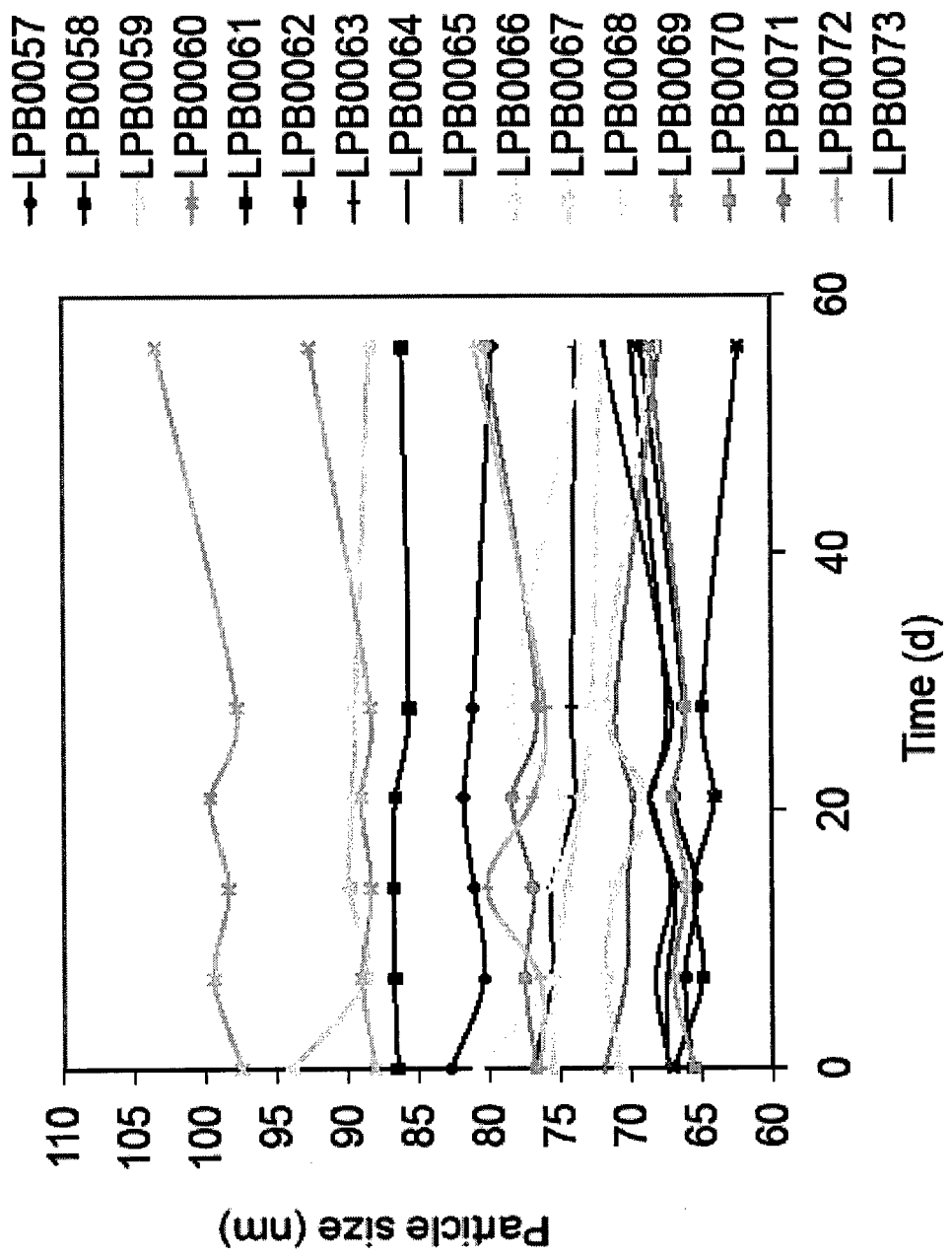
FIG. 3.
Change in particle size during storage at 2-8° C. for LPB0057-LPB0073 FIG. 4.
Change in PDI during storage at 2-8° C. for LPB0057-LPB0073
Figure 4:
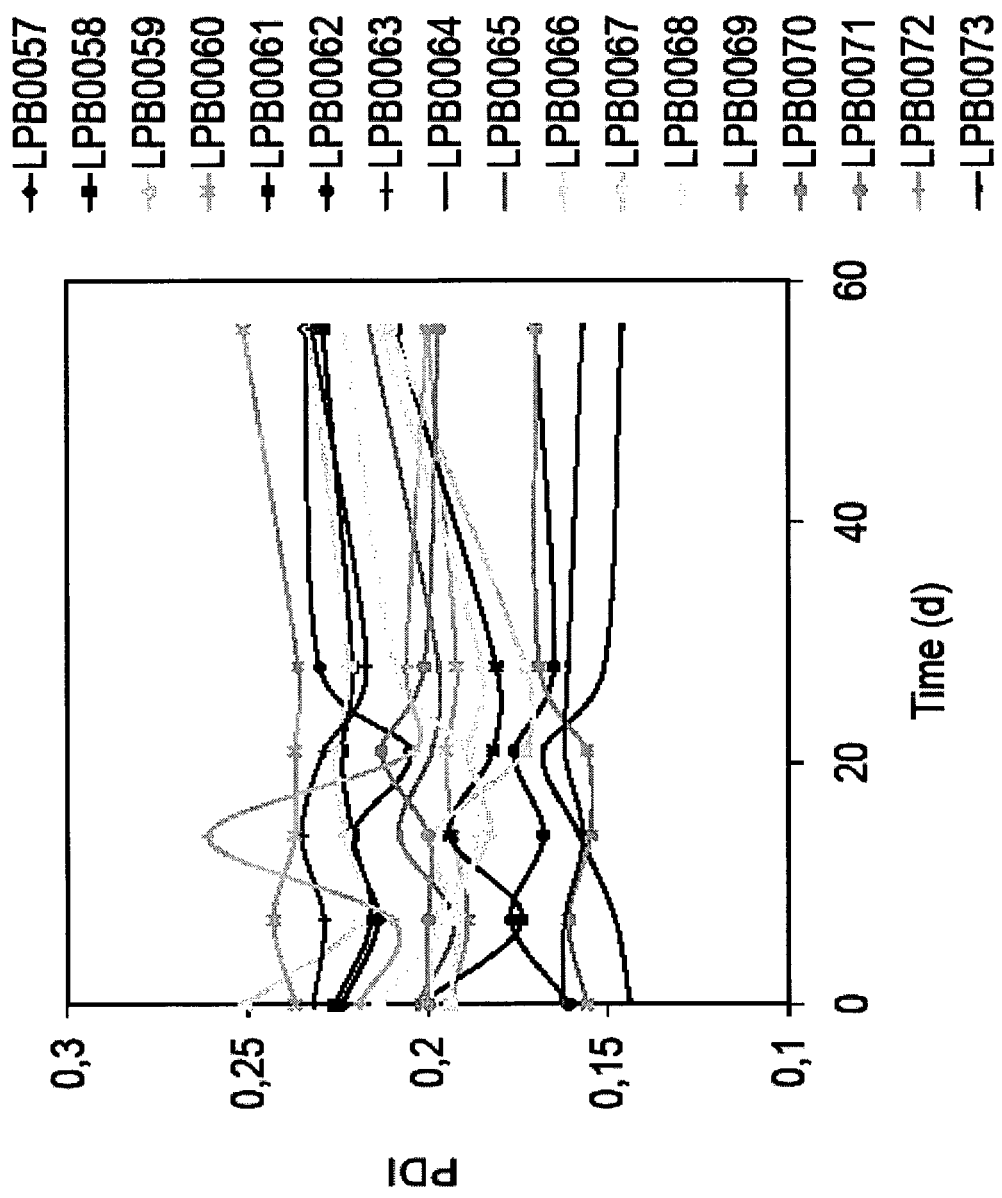

Changes in particle size and PDI during storage are presented in FIG. 3-4. No significant changes in particle size were observed during cold storage for any of the liposomal formulations prepared.

Initial Degree of Encapsulation (%)

Figure 5:
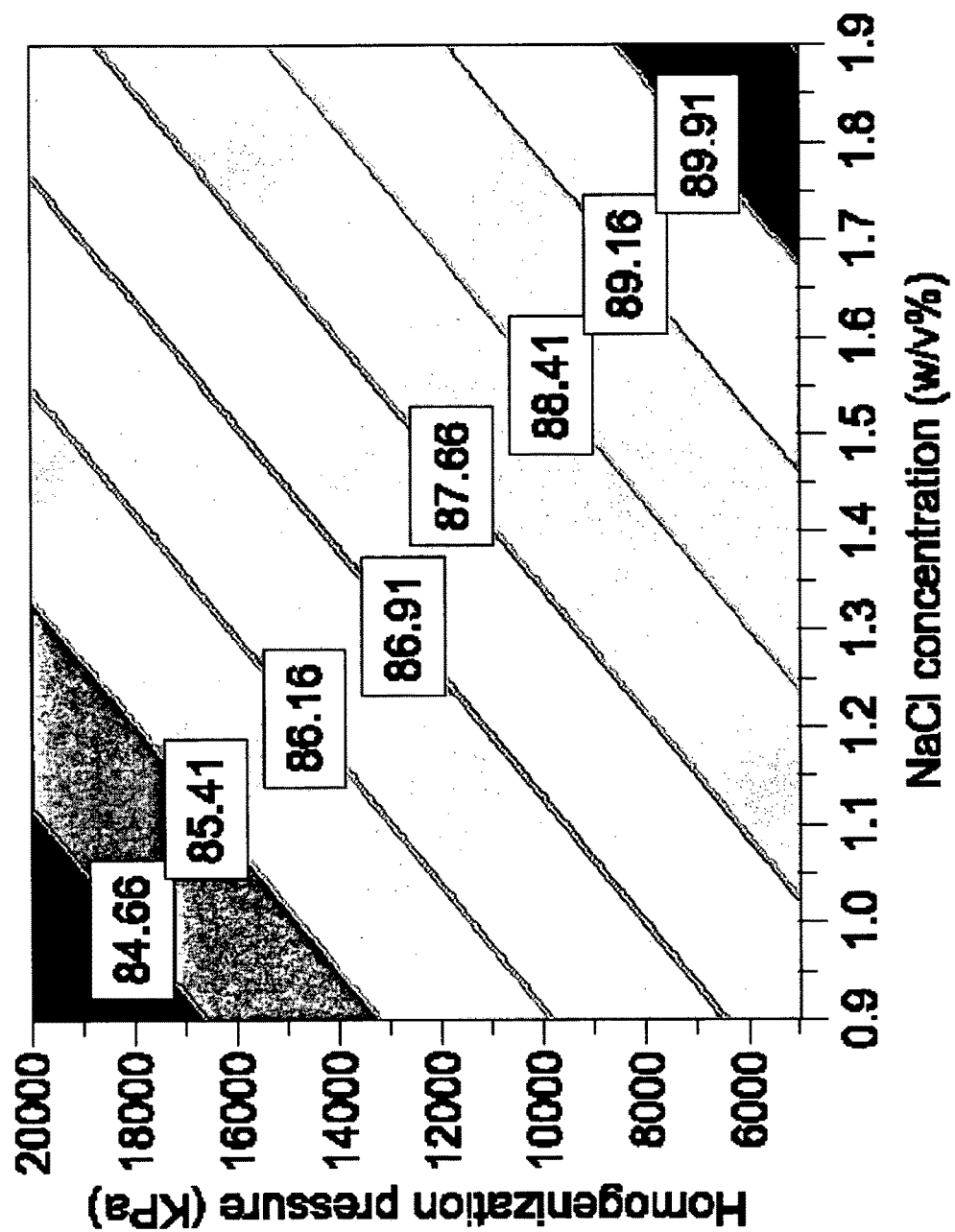
FIG. 5.
Contour plot illustrating the influence of interior NaCl concentration and homogenization pressure used during liposome preparation on initial DOE %. Numbers inside the contour plot indicate DOE %.

Formulations had an initial degree of encapsulation ranging from 84 to 92%. It was demonstrated that NaCl had the most significant influence on the initial degree of encapsulation (DOE). With a higher salt concentration used in the hydration solution a higher initial DOE was obtained. Furthermore higher homogenization pressure used during preparation resulted in lower DOE. This is probably due to the fact that smaller liposomes are obtained at higher homogenization pressure, and thus more platinum can be expected on the liposome exterior. Contour illustrating the influence of interior NaCl concentration and homogenization pressure used during liposome preparation on initial DOE % is presented in FIG. 5.

Figure 6:
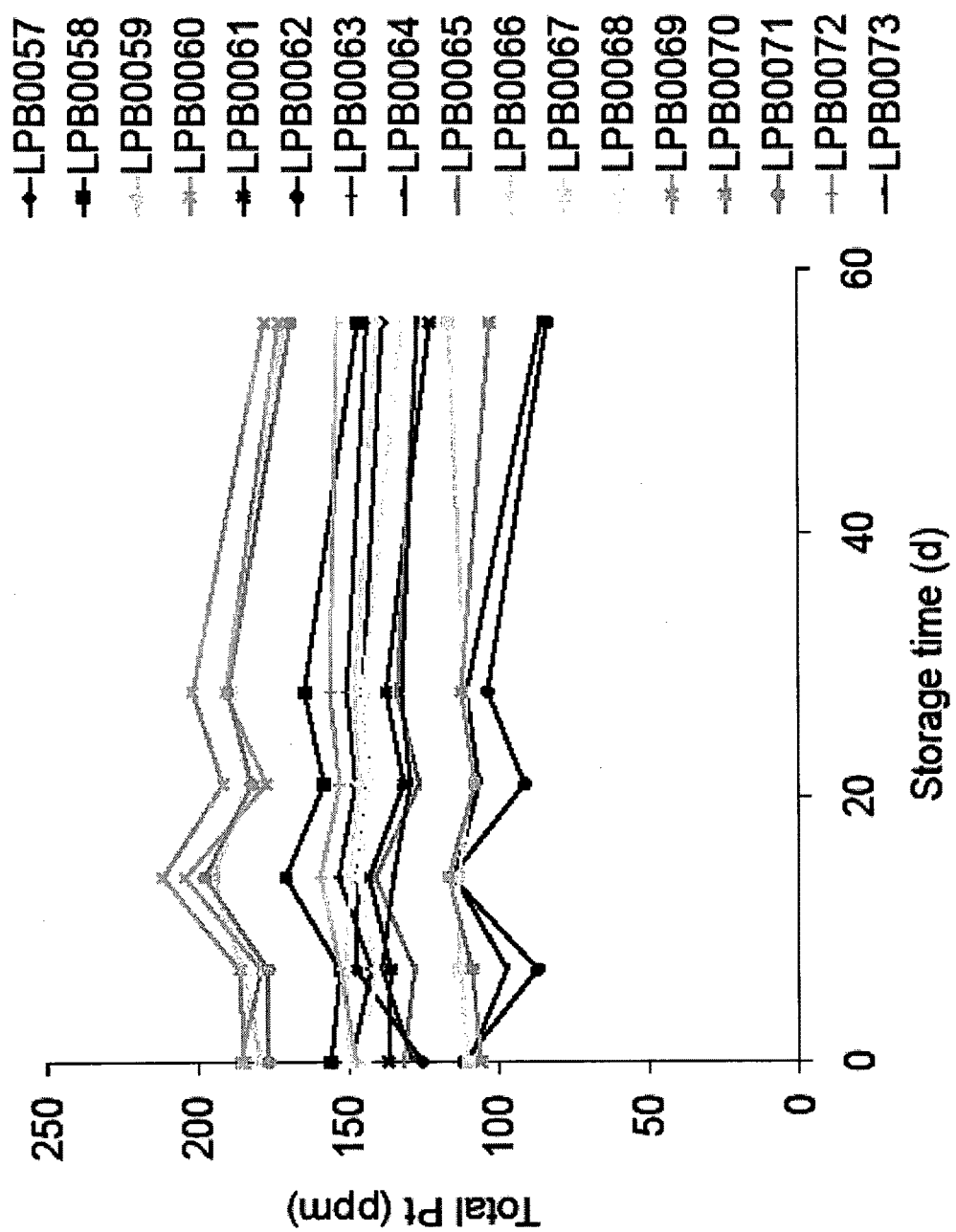
FIG. 6.
Pt concentration during storage for LPB0057-LPB0073.
Figure 7:
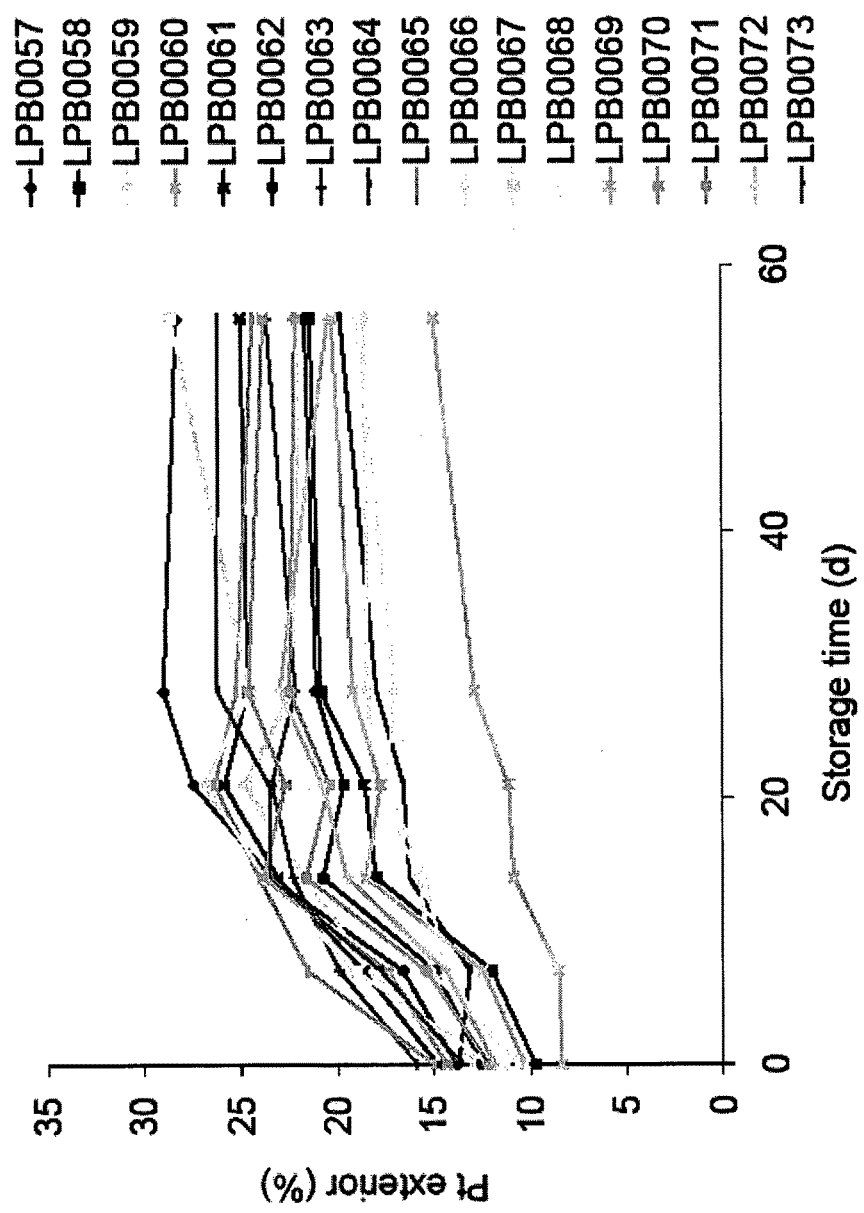
FIG. 7.
Pt exterior (%) during storage for LPB0057-LPB0073.
Figure 8:
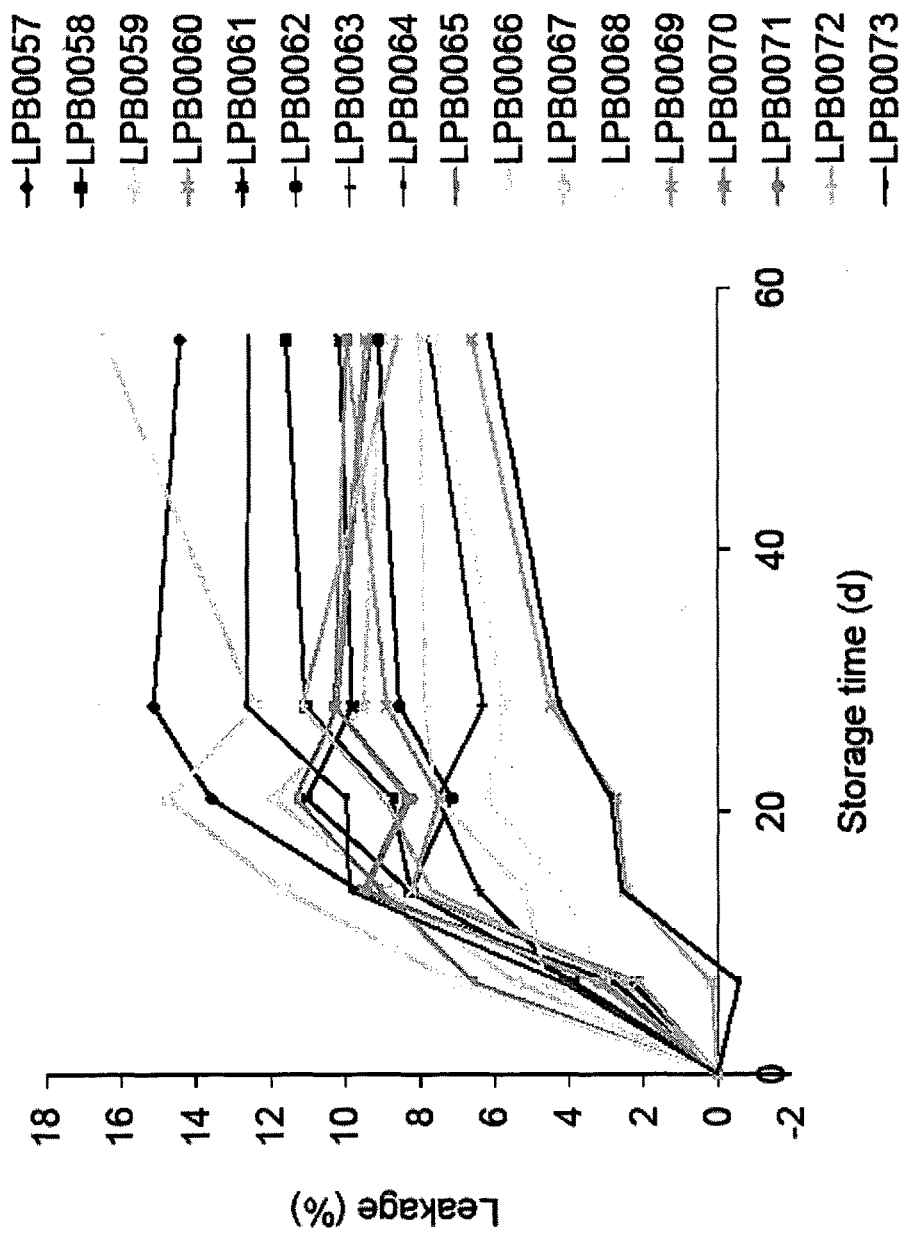
FIG. 8.
Leakage from LPB0057-LPB0073 during storage at 2-8° C.
Figure 9:
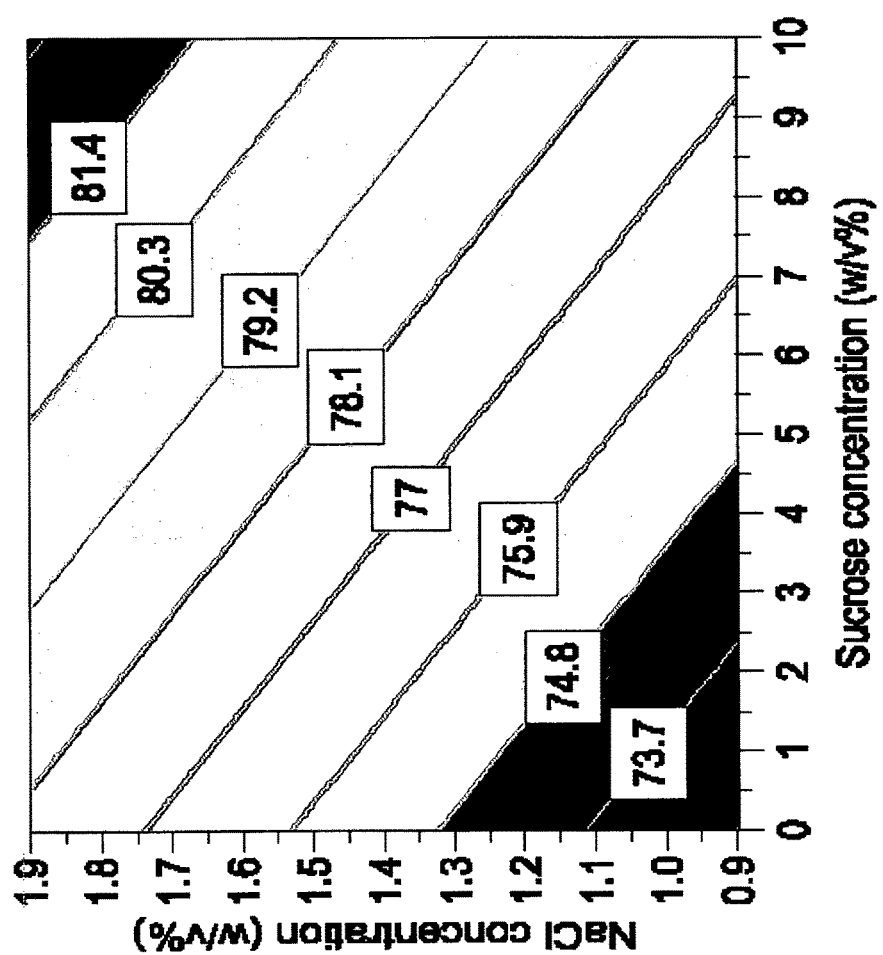
FIG. 9.
Contour plot illustrating the influence of interior NaCl concentration and sucrose concentration on DOE % after 56d storage at 2-8° C. with homogenization pressure maintained at 12,500 KPa. Numbers inside the contour plot indicate DOE % after 56d storage at 2-8° C.
Figure 10:
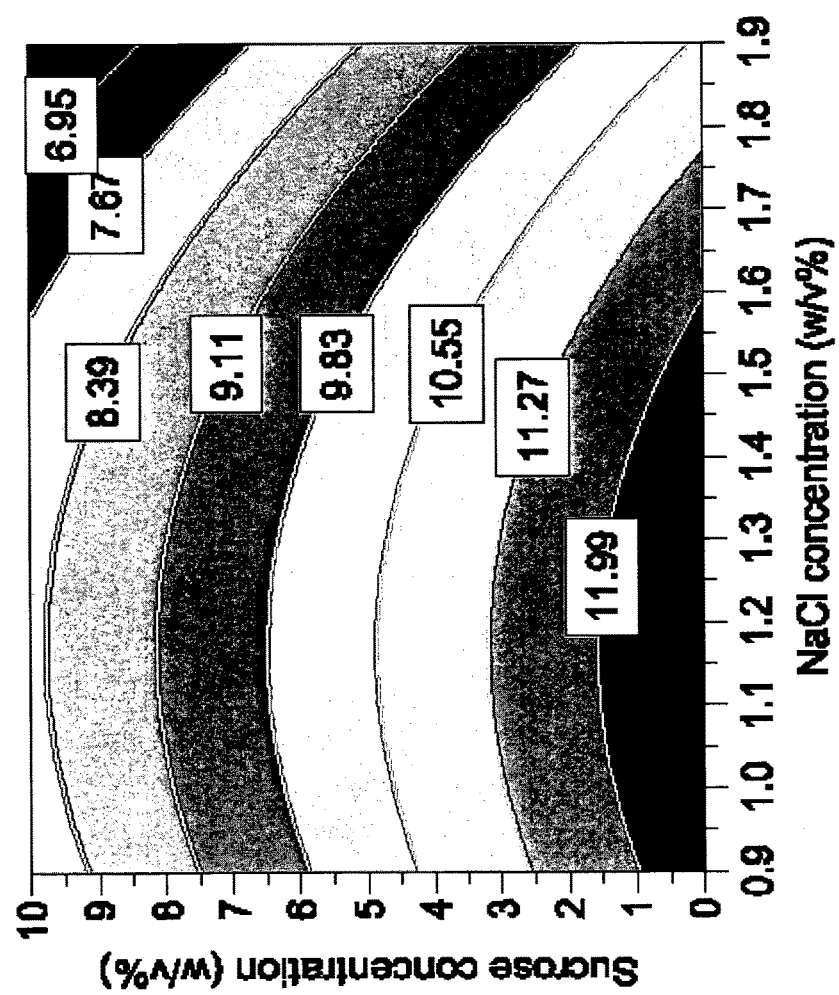
FIG. 10.
Contour plot illustrating the influence of interior NaCl concentration and sucrose concentration on % Leakage after 56d storage at 2-8° C. with homogenization pressure maintained at 12,500 KPa. Numbers inside the contour plot indicate % Leakage after 56d storage at 2-8° C.

Influence of parameters on DOE % and leakage after 56 d storage at 2-8° C. Pt analysis (total Pt content, liposome exterior Pt content and leakage) during storage are presented in FIG. 6-8.

It was demonstrated that interior NaCl and sucrose concentrations have significant influence on degree of encapsulation (DOE) after 56 d storage. With a higher NaCl and sucrose concentration on the liposome interior a higher DOE was obtained. No main effect was observed for homogenization pressure; however interaction between homogenization pressure and sucrose was seen. At high interior sucrose concentration and a low homogenization pressure results in higher DOE compared, as compared to having higher homogenization pressure.

The amount of cisplatin leaking from the formulation during 56d storage depends on all factors examined. However the factor having the most significant effect on leakage was sucrose concentration. Increasing interior NaCl and sucrose concentrations were observed to increase drug retention during storage. More leakage could be observed from liposomes prepared at low pressure compared to those prepared at higher pressure.

Lowest leakage was observed for formulations prepared with hydration solution containing 10% sucrose and 1.9% NaCl, and homogenized at 20000 KPa. The formulation having the highest DOE after 56d storage at 2-8° C. was prepared with hydration solution containing 10% sucrose and 1.9% NaCl, and homogenized at 5000 KPa.

Conclusion

The response models satisfactorily expressed the relationship between the selected parameters and the responses. The results demonstrate that interior NaCl and sucrose concentrations have significant influence on the leakage from LiPlacis formulation during storage at 2-8° C. During storage the factor having the most significant influence on drug retention was sucrose. Increasing NaCl also improves drug retention. Highest encapsulation degree after 56d was seen for formulations having high NaCl and sucrose concentration on the liposome interior. DOE was demonstrated to be improved by increasing NaCl concentration in the hydration media.

Leakage was most pronounced when liposomes were prepared at low pressure, as compared to liposomes prepared at high pressure. Initial DOE is also higher for liposomes prepared at lower pressures. Since the homogenization pressure has a major influence on the particle size the results indicate that drug retention is to some extent influenced by particle size. i The formulations having the highest degree of encapsulation after two months of storage was prepared with 1.9% NaCl and 10% sucrose on the liposome interior, and homogenized at low pressure.

No significant changes in particle size were seen during storage for any of the formulations prepared.

Example 2

Liposomal cisplatin formulations were prepared by film hydration followed by extrusion. Hydration solution was prepared with varying osmolyte concentrations. After extrusion the liposomes were dialyzed in different media. The formulations prepared had different osmotic gradient (difference in osmolarity between interior and exterior) as outlined in table 3. For comparison liposomal formulation of other chemotherapeutics were prepared as outlined in table 4. All Formulations were placed in refrigerator at 2-8° C., and samples were taken continually during storage.

Preparation of Liposomal Formulations

Phospholipids (DSPC/DSPG/DSPE-PEG2000, 70:25:5 mol %) were dissolved in 9:1 (v/v) chloroform/methanol. The solvent of the dissolved lipid mixtures were then evaporated in a 50° C. hot water bath until visual dryness, under a stream of nitrogen gas. The samples were further dried under vacuum overnight.

Hydration liquids (varying Salt and sucrose concentrations according to table 3 and 4) containing a chemotherapeutic were added to the dried lipid mixtures at a temperature of 65° C. for the preparation of multilamellar vesicles (MLV). The lipid suspensions were kept at 65° C. for at least 30 min. in order to ensure complete hydration. During this period, the lipid suspensions were vortex every 5 min. Large unilamellar vesicles (LUV) were prepared by extrusion through membranes with defined pore size (100 nm) at 65° C. LUV were subsequently transferred to dialysis cassettes (MWCO: 10 kDa) in order to remove un-entrapped drug. Liposomal formulations were dialyzed in different buffer solutions as outlined in table 3 and 4.

Immediately after preparation the formulations were divided into glass vials. Glass vials were sealed with cap and placed in refrigerator (2-8° C.). The day of placement in refrigerator is considered as the initiation date. Sampled were taken continually during storage, and particle size and drug concentration (Exterior and total) was determined.

Results:

Liposomal formulations were prepared with either cisplatin, oxaliplatin, MTX, Bleomycin, or 5FU. Formulations containing small molecular weight drug (<350 g/mol) such as cisplatin and 5FU was observed to be leaky when osmotic gradient between interior and exterior was low. Liposomal formulations containing drugs with higher molecular weight (>350 g/mol) were demonstrated to be practically non-leaky during storage at 2-8° C.

Figure 11:
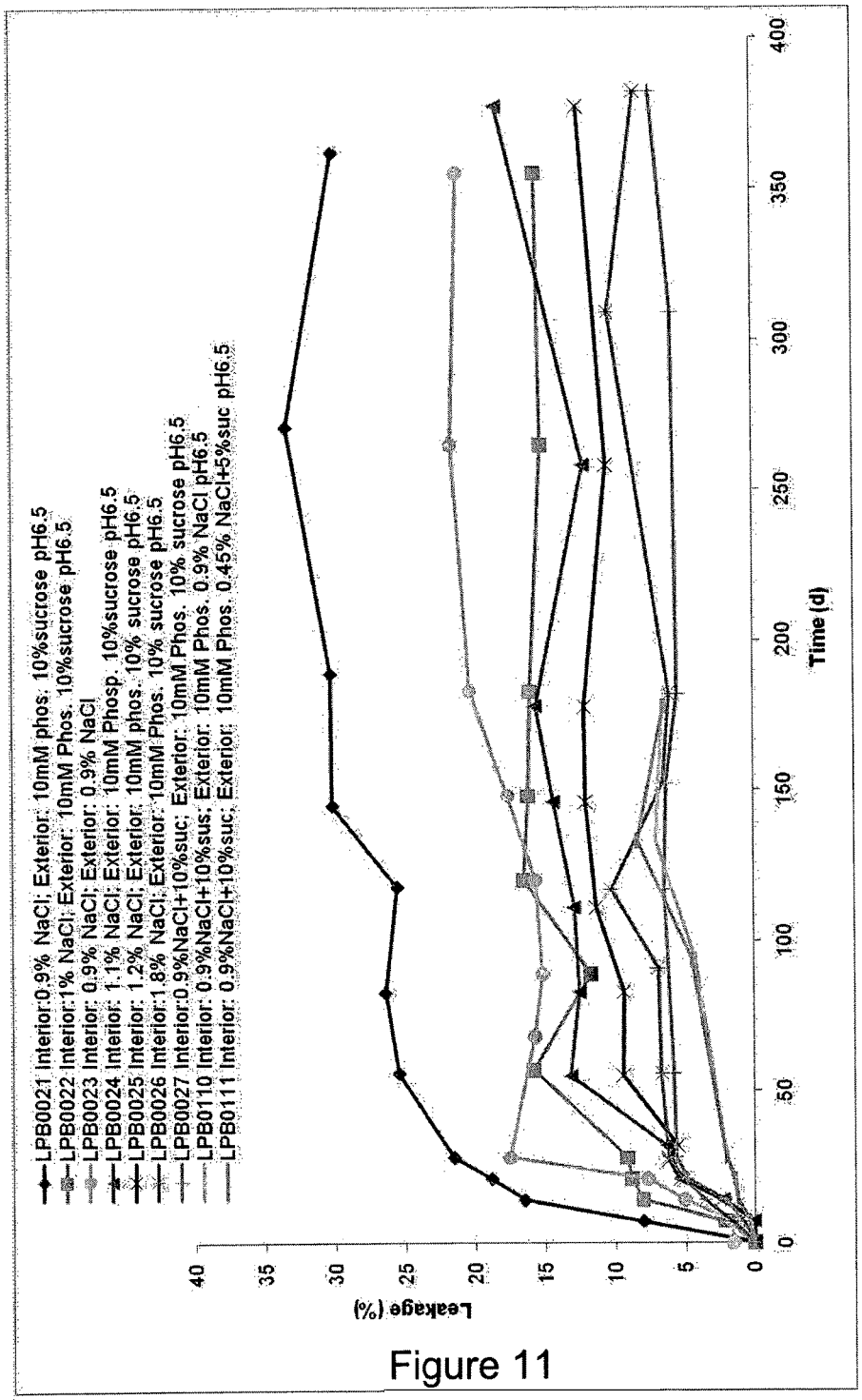
FIG. 11.
Leakage from liposomal cisplatin formulation during storage at 2-8° C. Formulations were prepared with varying osmotic gradient. For further details refer to table 3.

Trials to increase the osmotic gradient in cisplatin formulations were demonstrated to be an effective way to minimize the leakage during storage. When the difference between the interior and exterior osmotic gradient was >282 mOsM, the leakage observed during storage was maintained at acceptable levels (see table 3 and FIG. 11).

Figure 12:
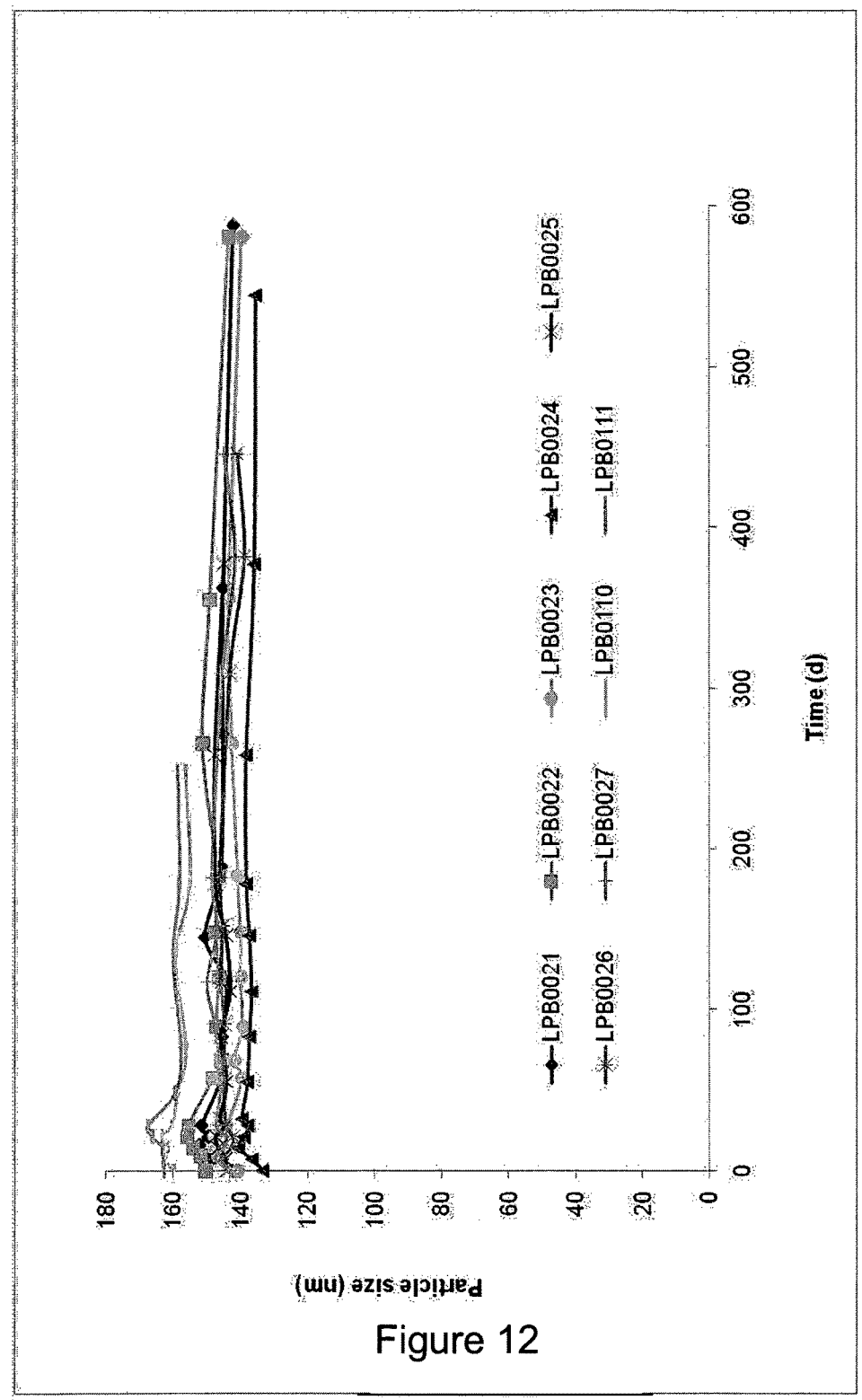
FIG. 12.
Particle size of liposomal cisplatin formulations during storage at 2-8° C. For detailed description about the buffer composition refer to table 3.

No changes in particle size were observed in particle size during storage at 2-8° C. (FIG. 12). The particle size of the formulation is thus not influenced by higher osmotic gradient in the cisplatin formulation.

The invention claimed is:

1. A pharmaceutical composition comprising:
   (a) a secretory phospholipase $A_2$ (sPLA$_2$) hydrolysable liposome comprising distearoyl phosphatidyl glycerol (DSPG) in an amount of 20% to 45% (mol/mol), distearoyl phosphatidyl choline (DSPC) in an amount of 40% to 75% (mol/mol), [poly(ethylene glycol)]-distearoyl phosphatidyl ethanolamine (DSPE-PEG) in an amount of 3% to 6% (mol/mol), less than 1% cholesterol, and cisplatin encapsulated in the liposome as a therapeutic agent,
   (b) an exterior solution, and
   (c) an interior solution within the liposome,
   wherein a difference in osmolyte concentration between the interior solution and the exterior solution is greater than 200 mOsm, wherein the difference in osmolyte concentration is the exterior solution osmolyte concentration subtracted from the interior solution osmolyte concentration.

2. The pharmaceutical composition of claim 1, wherein the only therapeutic agent is cisplatin.

3. The pharmaceutical composition of claim 1, wherein the difference in osmolyte concentration between the interior solution and the exterior solution is between 200 mOsm and 600 mOsm.

4. The pharmaceutical composition of claim 1, wherein the difference in osmolyte concentration between the interior solution and the exterior solution is between 280 mOsm and 320 mOsm.

5. The pharmaceutical composition of claim 1, wherein the difference in osmolyte concentration between the interior solution and the exterior solution is at least 275 mOsm.

6. The pharmaceutical composition of claim 1, wherein the interior solution comprises NaCl or KCl at a concentration between 0.2 to 2.5% w/w.

7. The pharmaceutical composition of claim 1, wherein the exterior solution comprises NaCl or KCl at a concentration between 0.2 to 2.5% w/w.

8. The pharmaceutical composition of claim 1, wherein the interior solution and the exterior solution are selected from the group consisting of:
   (a) Interior solution of 0.8% to 1.0% NaCl and 9% to 11% sucrose and exterior solution of 8 mM to 12 mM phosphate buffer (pH 6.5) and 9% to 11% sucrose,
   (b) Interior solution of 1.6% to 2.0% NaCl and exterior solution of 8 mM to 12 mM phosphate buffer (pH 6.5) and 9% to 11% sucrose,
   (c) Interior solution of 0.8% to 1.0% NaCl and 9% to 11% sucrose and exterior solution of 0.35% to 0.55% NaCl and 4% to 6% sucrose, and
   (d) Interior solution of 0.8% to 1.0% NaCl and 9% to 11% sucrose and exterior solution of 8 mM to 12 mM phosphate buffer (pH 6.5) and 0.8% to 1.0% NaCl.

9. The pharmaceutical composition of claim 1, wherein the liposome comprises an additional therapeutic agent.

10. The pharmaceutical composition of claim 1, wherein the liposome comprises DSPG in an amount of 25% (mol/mol), DSPC in an amount of 70% (mol/mol), DSPE-PEG in an amount of 5% (mol/mol), and less than 1% cholesterol.

11. The pharmaceutical composition comprising more than one of said liposome of claim 1.

12. The pharmaceutical composition of claim 1, wherein leakage of cisplatin from the liposome is reduced relative to the liposome having a difference in osmolyte concentration between the interior solution and the exterior solution of less than 200 mOsm.

* * * * *

UNITED STATES PATENT AND TRADEMARK OFFICE
CERTIFICATE OF CORRECTION

PATENT NO. : 9,820,941 B2
APPLICATION NO. : 13/503614
DATED : November 21, 2017
INVENTOR(S) : Mogens Winkel Madsen et al.

Page 1 of 1

It is certified that error appears in the above-identified patent and that said Letters Patent is hereby corrected as shown below:

On the Title Page

Item (74) under *Attorney, Agent, or Firm*, replace "Kristina Bicker-Brady" with --Kristina Bieker-Brady--.

Signed and Sealed this
Twenty-third Day of January, 2018

Joseph Matal
*Performing the Functions and Duties of the
Under Secretary of Commerce for Intellectual Property and
Director of the United States Patent and Trademark Office*